United States Patent
Ka-Yiu et al.

(10) Patent No.: US 7,262,046 B2
(45) Date of Patent: *Aug. 28, 2007

(54) AEROBIC SUCCINATE PRODUCTION IN BACTERIA

(75) Inventors: San Ka-Yiu, Houston, TX (US); George N. Bennett, Houston, TX (US); Henry Lin, Houston, TX (US)

(73) Assignee: Rice University, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/200,385

(22) Filed: Aug. 9, 2005

(65) Prior Publication Data

US 2006/0040368 A1 Feb. 23, 2006

Related U.S. Application Data

(60) Provisional application No. 60/599,956, filed on Aug. 9, 2004.

(51) Int. Cl.
- C12N 1/20 (2006.01)
- C12N 1/12 (2006.01)
- C12N 15/00 (2006.01)
- C12N 15/74 (2006.01)
- C12P 7/48 (2006.01)
- C12P 4/46 (2006.01)

(52) U.S. Cl. ............ 435/252.33; 435/144; 435/145; 435/252.1; 435/252.3; 435/440; 435/471; 435/488

(58) Field of Classification Search ................. None
See application file for complete search history.

(56) References Cited

U.S. PATENT DOCUMENTS 6,743,610 B2 * 6/2004 Donnelly et al. ........... 435/145

OTHER PUBLICATIONS

Hong et al., 2001, Biotechhnol. Bioeng 74:89-95.*
Mijts et al (2003, current opinion in Biotechnology 14:597-602.*
Kubo et al., 2000, J. Biosc. Bioeng. 6:619-624.*
sunnarborg et al., 1990, J. Bacteriol. 172:2642-2649*
Abdel-hamid et al., 2001, microbial. 147:1483-1498.*
Yang et al., 2001, Metabolic engineering. 3:115-123.*
Helling et al., 1971, J. Bact. 105;1224-1226.*
Vemuri et al., 2002, J. Ind. Microbiol. Biotechnol 28:325-332.*
Yang et al., 2001, Biotechnol. Bioeng 65:291-297.*
Tseng et al., 2001, J. Bacteriol 183:461-467.*
Bramer et al., 2002, FEMS Microbiology Letters 212: 159-164.*
Cecchini, et al., (Bray, et al., eds) pp. 555-558, Walter de Gruyter, New York (1984).
Wang, et al. App. Biochem. Biotechnol. 70-72:919-28 (1998).

(Continued)

*Primary Examiner*—Sumesh Kaushal
*Assistant Examiner*—Kelaginamane T. Hiriyanna
(74) *Attorney, Agent, or Firm*—Baker & McKenzie LLP

(57) ABSTRACT

Methods of increasing yields of succinate using aerobic culture methods and a multi-mutant *E. coli* strain are provided. Also provided is a mutant strain of *E. coli* that produces high amounts of succinic acid.

4 Claims, 11 Drawing Sheets

OTHER PUBLICATIONS

Zhang, et al. Sheng Wu Gong Cheng Xue Bao. 17:59-63 (2001).
U.S. Appl. No. 10/923,635, Aug. 20, 2004, San et al.
U.S. Appl. No. 10/987,511, Nov. 12, 2004, San et al.
U.S. Appl. No. 11/214,309, Aug. 29, 2005, San et al.
Amann, et al., Gene 69:301-15 (1988).
Berrios-Rivera SJ, Bennett GN, San KY. Metabolic engineering of *Escherichia coli*: increase of NADH availability by overexpressing an NAD(+)-dependent formate dehydrogenase. Metab. Eng. Jul. 2002;4(3):217-29.
Carole, et al. Appl Biochem Biotechnol. 113-116:871-85 (2004).
Chan and Sim, Microbiology 144:3229-37 (1998).
Chang, et al. Appl Environ Microbiol. 65:1384-9 (1999).
Chatterjee, et al. Appl Environ Microbiol. 67:148-54 (2001).
Chou, C., et al.; Effect of Modulated Glucose Uptake on High-Level Recombinant Protein Production in a Dense *E. coli* Culture; Biotechnol. Prog., vol. 10, pp. 644-647, 1994.
Datsenko and Wanner. Proc Natl Acad Sci U S A. 97:6640-5 (2000).
Dittrich, C. R.; Vadali, R. V.; Bennett, G. N. San, K.-Y. Redistribution of metabolic fluxes in the central aerobic metabolic pathway of *E.coli* mutant strains with deletion of the ackA-pta and poxB pathways for the production of isoamyl acetate. 2004.
Fiegler, et al., J. Bact. 181:4929-36 (1999).
Gokarn, et al., App. Micobiol. Biotechnol. 56:188-95 (2001).
Gokarn, R. R.; Eiteman, M. A.; Altman, E. Expression of pyruvate carboxylase enhances succinate production in *Escherichia coli* without affecting glucose uptake rate. Biotech. let. 1998, 20, 795-798.
Gokarn, R. R.; Eiteman, M. A.; Altman, E. Metabolic analysis of *Escherichia coli* in the presence and absense of carboxylating enzymes phosphoenolpyruvate carboxylase and pyruvate carboxylase. App Environ Microbiol. 2000, 666, 1844-1850.
Goldberg, et al., App. Environ. Microbiol. 45:1838-47 (1983).
Hahm, D. H.; Pan, J. G.; Rhee, J. S. Characterization and evaluation of a pta (phosphotransacetylase) negative mutant of *Escherichia coli* HZB101 as a production host of foreign lipase. Appl Microbiol Biotechnol. 1994, 42, 100-107.
Hasona, et al. J Bact. 186:7593-600 (2004).
Holms, W. H. The central metabolic pathways in *Escherichia coli*: relationship between flux and control at a branchpoint, efficiency of conversion to biomass, and excretion of acetate. Curr Top Cell Regul. 1986, 28, 69-105.
Kelly, et al., Microbiology 148:793-8 (2002).
Kern, et al., FEMS Yeast Research. 5:43-9 (2004).
Kim, et al. Appl Environ Microbiol. 70:1238-41 (2004).
Kornberg, H. L. The role and control of the glyoxylate cycle in *Escherichia coli*. Biochem. J. 1966, 99, 1-11.
Lin H, Bennett GN, San KY. Effect of carbon sources differing in oxidation state and transport route on succinate production in metabolically engineered *Escherichia coli*. J Ind Microbiol Biotechnol. Mar. 16, 2005; 32: 87-93.
Lin H, Bennett GN, San KY. Genetic reconstruction of the aerobic central metabolism in *Escherichia coli* for the absolute aerobic production of succinate. Biotechnol Bioeng. Jan. 20, 2005;89(2):148-56.
Lin H, San KY, Bennett GN. Effect of Sorghum vulgare phosphoenolpyruvate carboxylase and Lactococcus lactis pyruvate carboxylase coexpression on succinate production in mutant strains of *Escherichia coli*.Appl Microbiol Biotechnol. Nov. 24, 2004; pp. 1-16.
Lin H, Vadali RV, Bennett GN, San KY. Increasing the acetyl-CoA pool in the presence of overexpressed phosphoenolpyruvate carboxylase or pyruvate carboxylase enhances succinate production in *Escherichia coli*. Biotechnol Prog. Sep.-Oct. 2004;20(5):1599-604.
Lin H. et al. Metabolic engineering of aerobic succinate production systems in *Escherichia coli* to improve process productivity and achieve the maximum theoretical succinate yield. Metab Eng. Mar. 2005;7(2):116-27.
Lin, et al. Biotechnol. Bioeng. 90:775-9 (2005).
Luli, G. W.; Strohl, W. R. Comparison of growth, acetate production, and acetate inhibition of *Escherichia coli* strains in batch and fed-batch fermentations. Applied and Environmental Microbiology. 1990, 56, 1004-1011.
Maklashina, et al. J Bact. 180:5989-96 (1998).
Millard, et al.,. App. Environ. Microbiol. 62:1808-10 (1996).
Phillips, G. J.; Park, S. K.; Huber, D. High copy number plasmids compatible with commonly used cloning vectors. Biotechniques. 2000, 28, 400-408.
Samuelov, et al. Appl Environ Microbiol. 65:2260-3 (1999).
Sanchez, et al. Biotechnol. Prog. 21:358-65 (2005a).
Sanchez, et al. Metab Eng. 7:229-39 (2005b).
Stols and Donnelly App. Environ. Microbiol. 63:2695-701 (1997).
Tolentino et al., Biotech. Let. 14:157-62. (1992).
Underwood, et al., App. Environ. Microbiol. 68: 1071-81 (2002).
Varadarajan and Miller, Biotechnol. Prog. 15:845-854 (1999).
Vemuri, et al. J. Ind. Microbiol. Biotechnol. 28:325-32 (2002).
Vemuri, G. N.; Eiteman, M. A.; Altman, E. Effect of growth mode and pyrucate carboxylase on succinic acid production by metabolically engineered strains of *Escherichia coli*. Appl Environ Microbiol. 2002, 68, 1715-1727.
Volkert, et al., J. Bact. 176:1297-302 (1994).
Wang, et al., App. Environ. Microbiol. 66:1223-7 (2000).
Wang, et al., J. Biol. Chem. 267:16759-62. (1992).
Xu, et al. Appl. Microbiol. Biotechnol. 51:564-71 (1999).
Xu, et al., Biotechnol. Prog. 15:81-90 (1999).
Yang et al., Metab. Eng. 1, 141-152 (1999b).
Yang YT, Aristidou AA, San KY, Bennett GN. Metabolic flux analysis of *Escherichia coli* deficient in the acetate production pathway and expressing the *Bacillus subtilis* acetolactate synthase. Metab Eng. Jan. 1999;1(1):26-34.
Yang YT, Peredelchuk M, Bennett GN, San KY. Effect of variation of *Klebsiella pneumoniae* acetolactate synthase expression on metabolic flux redistribution in *Escherichia coli*. Biotechnol Bioeng. Jul. 20, 2000; 69(2):150-9.
Yang, et al. Biotechnol. Bioeng. 65:291-7 (1999).
Yanisch-Perron, et al., Gene 33:103-19 (1985).
Zeikus, et al., App. Microbiol. Biotechnol. 51:545-52 (1999).

* cited by examiner

AEROBIC SUCCINATE PRODUCTION IN BACTERIA

PRIOR RELATED APPLICATIONS

This application claims the benefit under 35 USC §119(e) to U.S. Provisional Application Ser. No. 60/599,956 filed Aug. 9, 2004, entitled "Aerobic Succinate Production In Bacteria," which is incorporated herein in its entirety.

FEDERALLY SPONSORED RESEARCH STATEMENT

The present invention was developed with funds from the National Science Foundation and the U.S. Department of Agriculture. Therefore, the United States Government may have certain rights in the invention.

REFERENCE TO MICROFICHE APPENDIX

Not applicable.

REFERENCE TO A SEQUENCE LISTING

Not applicable.

FIELD OF THE INVENTION

The invention relates to methods of producing succinic acid, malic acid, fumaric acid, and other carboxylic acids in metabolically engineered microorganisms.

BACKGROUND OF THE INVENTION

The valuable specialty chemical succinate and its derivatives have extensive industrial applications. Succinic acid is used as a raw material for food, medicine, plastics, cosmetics, and textiles, as well as in plating and waste-gas scrubbing (66). Succinic acid can serve as a feedstock for such plastic precursors as 1,4-butanediol (BDO), tetrahydrofuran, and gamma-butyrolactone. Further, succinic acid and BDO can be used as monomers for polyesters. If the cost of succinate can be reduced, it will become more useful as an intermediary feedstock for producing other bulk chemicals (51). Along with succinic acid, other 4-carbon dicarboxylic acids such as malic acid and fumaric acid also have feedstock potential.

Currently, succinate is produced through petrochemical processes that are expensive and can damage the environment. A high yield succinate producing bacteria would allow replacement of a petroleum product with a feedstock that uses agricultural waste. The production of succinate, malic acid, and fumaric acid from glucose, xylose, sorbitol and other "green" sources by *Escherichia coli* provides a low cost renewable source of chemical feedstocks. Additionally, heterologous genes are often expressed in *E. coli* to produce valuable compounds such as polyketides, esters, nutritional compounds, and pigments.

Metabolic engineering has the potential to considerably improve process productivity by manipulating the throughput of metabolic pathways. Specifically, manipulating enzyme levels through the amplification, addition, or reduction of a particular pathway can result in high yields of a desired product. Various genetic improvements for succinic acid production under anaerobic conditions have been described that utilize the mixed-acid fermentation pathways of *E. coli*. Examples include the overexpression of phoenolpyruvate carboxylase (pepc) from *E. coli* (38). The conversion of fumarate to succinate was improved by overexpressing native fumarate reductase (frd) in *E. coli* (16, 57). Certain enzymes are not indigenous in *E. coli*, but can potentially help increase succinate production. By introducing pyruvate carboxylase (pyc) from *Rhizobium* etli into *E. coli*, succinate production was enhanced (13, 14, 15). Other metabolic engineering strategies also include inactivating competing pathways of succinate. When malic enzyme was overexpressed in a host with inactivated pyruvate formate lyase (pfl) and lactate dehydrogenase (ldh) genes, succinate became the major fermentation product (45, 21). In cultures of this pfl and ldh mutant strain, there is a large pyruvate accumulation. Overexpression of malic enzyme in this mutant strain increased succinate production driven by the high pyruvate pool toward the direction of malate formation, which subsequently was converted to succinate. An inactive glucose phosphotransferase system (ptsG) in the same mutant strain (pfl$^-$ and ldh$^-$) had also been shown to yield higher succinate production in *E. coli* and improve growth (8). Unfortunately, anaerobic fermentation is hampered by the limited NADH availability, poor biomass generation, slow carbon throughput, and, therefore, slow product formation.

Because of the disadvantages of anaerobic fermentation, *E. coli* was genetically engineered to produce succinate under aerobic conditions (29, 34). This work provides metabolically engineered succinate production systems that can operate under aerobic conditions through pathway modeling, optimization, and genetic engineering of the aerobic central metabolism. This is the first platform for enhancing succinate production aerobically in *E. coli* based on the creation of a new aerobic central metabolic network.

SUMMARY OF THE INVENTION

A mutant bacterial strain with more than three pathway genes inactivated to improve carboxylic acid production under aerobic conditions is described wherein the carboxylic acid produced is succinate, fumarate, malate, oxaloacetate, or glyoxylate. In one embodiment of the invention, the genes sdhAB, (ackA-pta), poxB, iclR, and ptsG are inactivated. In another embodiment of the invention various combinations of genes are inactivated including sdhAB, (ackA-pta), poxB, iclR, and ptsG. These mutant strains can also be combined with the overexpression of PEPC, ACEA, ACEB, or ACEK to further increase succinate yield.

The mutant strains designated HL267k, HL2671k, HL26715k, HL27615k, HL12675k, HL51267k, HL51276k, HL52167k, HL52176k, HL512769k, HL2765k, HL27659k, HL51276k(pKK313), HL512769k(pKK313), HL2765k (pKK313), HL27659k(pKK313), HL51276k(pKK313C), HL512769k(pKK313C), HL2765k(pKK313C), HL27659k (pKK313C), HL276k, HL2761k, HL2765k, HL27659k, HL512k, HL5127k, HL51276k, HL126k, HL1267k, HL5126k, HL521k, HL5216k, and HL5217k, provide some embodiments of the invention.

Further, an aerobic method of producing carboxylic acids with a mutant bacterial strain is described, wherein said method comprises inoculating a culture with a mutant bacterial strain described above, culturing said culture under aerobic conditions, and isolating carboxylic acids from the media. Bacteria strains can be cultured in a flask, a bioreactor, a fed-batch bioreactor, or a chemostat bioreactor to obtain carboxylic acids.

BRIEF DESCRIPTION OF THE DRAWINGS

The accompanying drawings which are incorporated in and constitute a part of this specification and together with the description, serve to explain the principles of the invention.

DESCRIPTION OF EMBODIMENTS OF THE INVENTION

Figure 1:
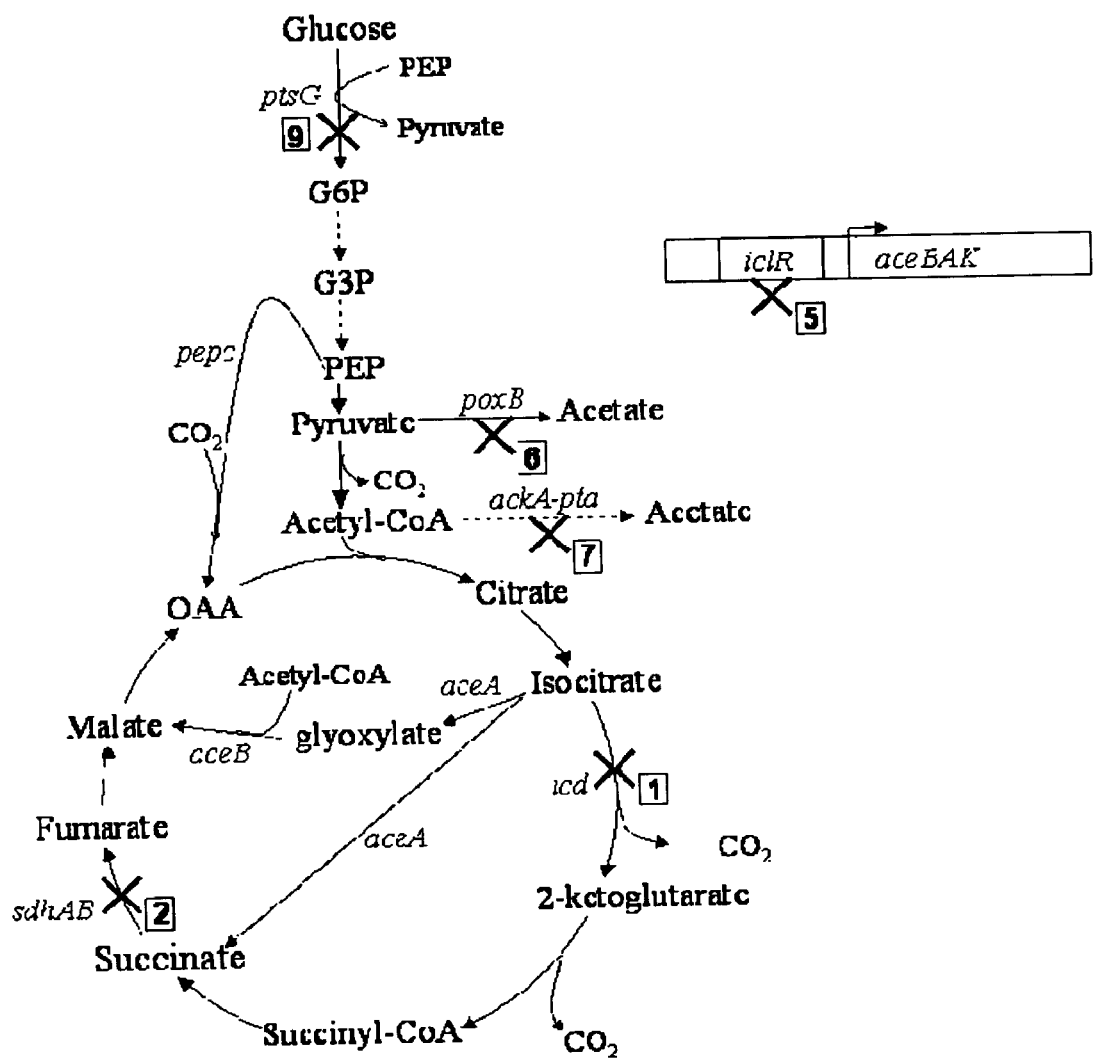
FIG. 1 Genetic Engineering of Glycolysis, TCA cycle, and Glyoxylate Bypass. 1 is a icd knockout, 2 is a sdhAB knockout, 5 is a iclR knockout, 6 is a poxB knockout, 7 is a ackA-pta knockout, and 9 is a ptsG knockout.

Carboxylic acids described herein can be a salt, acid, base, or derivative depending on structure, pH, and ions present. For example, the terms "succinate" and "succinic acid" are used interchangeably herein. Succinic acid is also called butanedioic acid ($C_4H_6O_4$). Chemicals used herein include formate, glyoxylate, lactate, malate, oxaloacetate (OAA), phosphoenolpyruvate (PEP), and pyruvate. Bacterial metabolic pathways including the Krebs cycle (also called citric acid, tricarboxylic acid, or TCA cycle) can be found in *Principles of Biochemistry*, by Lehninger as well as other biochemistry texts.

The terms "operably associated" or "operably linked," as used herein, refer to functionally coupled nucleic acid sequences.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation.

"Overexpression" or "overexpressed" is defined herein to be at least 150% of protein activity as compared with an appropriate control species. Overexpression can be achieved by mutating the protein to produce a more active form or a form that is resistant to inhibition. Overexpression can also be achieved by removing repressors, adding multiple copies of the gene to the cell, or upregulating the endogenous gene.

The terms "disruption" and "disruption strains," as used herein, refer to cell strains in which the native gene or promoter is mutated, deleted, interrupted, or down regulated in such a way as to decrease the activity of the gene. A gene can be completely (100%) reduced by knockout or removal of the entire genomic DNA sequence. Use of a frame shift mutation, early stop codon, point mutations of critical residues, or deletions or insertions can completely inactivate (100%) gene product by completely preventing transcription and/or translation of active protein.

As used herein "recombinant" is relating to, derived from, or containing genetically engineered material.

Genes are abbreviated as follows: isocitrate lyase (aceA a.k.a. icl); malate synthase (aceB); thy glyoxylate shunt operon (aceBAK); isocitrate dehydrogenase kinase/phosphorylase (aceK); acetate kinase-phosphotransacetylase (ackA-pta); alcohol dehydrogenase (adhE); aerobic respiratory control regulator A and B (arcAB); peroxide sensitivity (arg-lac); alcohol acetyltransferases 1 and 2 (atf1 and atf2); putative cadaverine/lysine antiporter (cadR); fatty acid degradation regulon (fadR); fumarate reductase (frd); fructose regulon (fruR); fumarase A, B, or C (fumABC); isocitrate dehydrogenase (icd); isocitrate lyase (icl); aceBAK operon repressor (iclR); lactate dehydrogenase (ldhA); malate dehydrogenase (mdh); phosphoenol pyruvate carboxylase (pepC); pyruvate formate lyase (pfl); pyruvate oxidase (poxB); phosphotransferase system genes F and G (ptsF and ptsG); pyruvate carboxylase (pyc); guanosine 3',5'-bispyrophosphate synthetase I (relAl); ribosomal protein S12 (rpsL); and succinate dehydrogenase (sdh). Δlac(arg-lac)205 (U169) is a chromosomal deletion of the arg-lac region that carries a gene or genes that sensitizes cells to $H_2O_2$ (55). The S8D mutation in *Sorghum pepc* advantageously relieves malate feedback inhibition of the PEPC protein (56).

Abbreviations: ampicillin (Ap); oxacillin (Ox); carbenicillin (Cn); chloramphenicol (Cm); kanamycin (Km); streptomycin (Sm); tetracycline (Tc); nalidixic acid (Nal); erythromycin (Em); ampicillin resistance ($Ap^R$); thiamphenicol/chloramphenicol resistance ($Thi^R/Cm^R$); macrolide, lincosamide and streptogramin A resistance ($MLS^R$); streptomycin resistance ($Sm^R$); kanamycin resistance ($Km^R$); Gram-negative origin of replication (ColE1); and Gram-positive origin of replication (OriII). Common restriction enzymes and restriction sites can be found at NEB® (NEW ENGLAND BIOLABS®, www.neb.com) and INVITROGEN® (www.invitrogen.com). ATCC®, AMERICAN TYPE CULTURE COLLECTION™ (www.atcc.org).

Plasmids and strains used in certain embodiments of the invention are set forth in Tables 1 and 2. GJT001, a spontaneous cadR mutant of MC4100, Δlac strain (arg-lac) U169 rspL150 relAl, is described in Tolentino (46). Pathway deletions were performed using P1 phage transduction and the one-step inactivation based on λ red recombinase (9). The construction of plasmids and mutant *E. coli* strains were performed using standard biochemistry techniques referenced herein and described in Sambrook (41) and Ausebel (2).

TABLE 1

Plasmids

| Plasmid | Genotype | Ref |
|---|---|---|
| pTrc99A | Cloning vector $Ap^R$ | 1 |
| pDHC29 | Cloning vector $Cm^R$ | 40 |
| pDHK29 | Cloning vector $Km^R$ | 40 |
| pUC19 | Cloning vector $Ap^R$ | 63 |
| pKK311 | Wildtype *Sorghum pepc* $Ap^R$ | 56 |
| pKK313 | S8D mutant *Sorghum pepc* $Ap^R$ | 56 |
| pKK313C | pKK313 Control vector with inactive *Sorghum pepc*, $Ap^R$ | 34 |
| pSMS1 | *S. clavuligerus* aceB $Km^R$ | 6 |
| pHL323 | Wildtype *Sorghum pepc* in pDHC29 $Cm^R$ | 29 |
| pHL333 | S8D mutant *Sorghum pepc* in pDHK29 $Km^R$ | 28 |

TABLE 2

Strains

| Strain | Genotype | Ref ATCC# |
|---|---|---|
| GJT001 | MC4100(ATC35695) cadR mutant Δlac(arg-lac)U169rpsL150relA1ptsF $Sm^R$ | 46 |
| HL2k | GJT001(sdhAB::$Km^R$) | 29 |
| HL26k | GJT001(sdhAB, poxB:: $Km^R$) | 29 |
| HL267k | GJT001(sdhAB, poxB, (ackA-pta):: $Km^R$) | 29 |
| HL2671k | GJT001(sdhAB, poxB, (ackA-pta), icd:: $Km^R$) | 29 |
| HL26715k | GJT001(sdhAB, poxB, (ackA-pta), icd, iclR:: $Km^R$) | 29 |
| HL27615k | GJT001(sdhAB, (ackA-pta), poxB, icd, iclR:: $Km^R$) | 29 |
| HL12675k | GJT001(icd, sdhAB, poxB, (ackA-pta), iclR:: $Km^R$) | 29 |
| HL51267k | GJT001(iclR, icd, sdhAB, poxB, (ackA-pta):: $Km^R$) | 29 |
| HL51276k | GJT001(iclR, icd, sdhAB, (ackA-pta), poxB:: $Km^R$) | 29 |
| HL52167k | GJT001(iclR, sdhAB, icd, poxB, (ackA-pta):: $Km^R$) | 29 |
| HL52176k | GJT001(iclR, sdhAB, icd, (ackA-pta), poxB:: $Km^R$) | 29 |
| HL512769k | GJT001(iclR, icd, sdhAB, (ackA-pta), poxB, ptsG:: $Km^R$) | 32 |
| HL2765k | GJT001(sdhAB, (ackA-pta), poxB, iclR:: $Km^R$) | 32 |
| HL27659k | GJT001(sdhAB, (ackA-pta), poxB, iclR, ptsG:: $Km^R$) | 32 |
| HL51276k (pKK313) | HL51276k overexpressing S8D mutant *Sorghum pepc* | 32 |
| HL512769k (pKK313) | HL512769k overexpressing S8D mutant *Sorghum pepc* | 32 |
| HL2765k (pKK313) | HL2765k overexpressing S8D mutant *Sorghum pepc* | 32 |
| HL27659k (pKK313) | HL27659k overexpressing S8D mutant *Sorghum pepc* | 32 |
| HL51276k (pKK313C) | HL51276k(pKK313) Control strain | 32 |
| HL512769k (pKK313C) | HL512769k(pKK313) Control strain | 32 |
| HL2765k (pKK313C) | HL2765k(pKK313) Control strain | 32 |
| HL27659k (pKK313C) | HL27659k(pKK313) Control strain | 32 |
| HL27k | GJT001(sdhAB, ackA-pta:: $Km^R$) | 29 |
| HL276k | GJT001(sdhAB, (ackA-pta), poxB:: $Km^R$) | 29 |
| HL2761k | GJT001(sdhAB, (ackA-pta), poxB, icd:: $Km^R$) | 29 |
| HL2765k | GJT001(sdhAB, (ackA-pta), poxB, iclR:: $Km^R$) | 32 |
| HL27659k | GJT001(sdhAB, (ackA-pta), poxB, iclR, ptsG:: $Km^R$) | 32 |
| HL5k | GJT001(iclR:: $Km^R$) | 29 |
| HL51k | GJT001(iclR, icd:: $Km^R$) | 29 |
| HL512k | GJT001(iclR, icd, sdhAB:: $Km^R$) | 29 |
| HL5127k | GJT001(iclR, icd, sdhAB, (ackA-pta):: $Km^R$) | 29 |
| HL51276k | GJT001(iclR, icd, sdhAB, (ackA-pta), poxB:: $Km^R$) | 29 |
| HL1k | GJT001(icd:: $Km^R$) | 29 |
| HL12k | GJT001(icd, sdhAB:: $Km^R$) | 29 |
| HL126k | GJT001(icd, sdhAB, poxB:: $Km^R$) | 29 |
| HL1267k | GJT001(icd, sdhAB, poxB, (ackA-pta):: $Km^R$) | 29 |
| HL5126k | GJT001(iclR, icd, sdhAB, poxB:: $Km^R$) | 29 |
| HL52k | GJT001(iclR, sdhAB:: $Km^R$) | 29 |
| HL521k | GJT001(iclR, sdhAB, icd:: $Km^R$) | 29 |
| HL5216k | GJT001(iclR, sdhAB, icd, poxB:: $Km^R$) | 29 |
| HL5217k | GJT001(iclR, sdhAB, icd, (ackA-pta):: $Km^R$) | 29 |

For general experiments under aerobic conditions, 250-ml flasks containing 50 ml of LB medium were used (41). The flasks were plugged with foam tube plugs to allow gas exchange with the environment. A seed inoculum of 200 μl from an overnight 5 ml culture was used for each flask. For succinate production under microaerobic conditions, 250-ml capped flasks containing 10 ml of medium were used. A seed inoculum of 40 μl from an overnight 5 ml culture was used for each flask. For bioreactor cultures, 5 ml overnight cultures were washed twice with fresh LB. The washed culture was then used to inoculate the bioreactor containing LB with 2 g/L $NaHCO_3$. This inoculum constituted less than 1% of the liquid volume in the bioreactor. Cultures were grown in bioreactors at 37° C. where the dissolved oxygen was maintained above 80% saturation throughout the experiment. For fed-batch reactors SB medium (2) with 2 g/L $NaHCO_3$ was used. The cultures were inoculated as described. Oxygen was maintained above 50% saturation throughout the experiment. Glucose was fed exponentially according to the specific growth rate of the strain studied. For chemostat bioreactors, LB medium with 2 g/l $NaHCO_3$ and 20 g/l of glucose was used. The cultures were inoculated as described. Chemostat experiments were performed under aerobic conditions at a dilution rate of 0.1 hr$^{-1}$. Oxygen was maintained above 50% saturation throughout the experiment.

EXAMPLE 1

Developing Aerobic Succinate Production Strains

Figure 8:
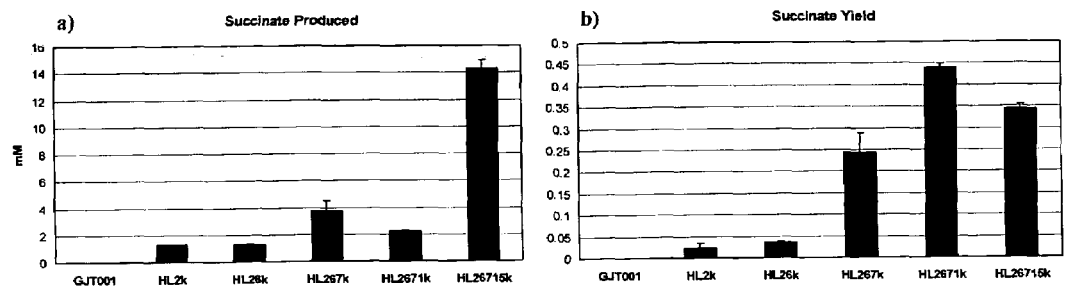
FIG. 8 Succinate Production. a) Succinate production at each incremental step of incorporating mutations into the parental strain. Each number designates a specific knockout in the pathways as shown by FIG. 1.; b) Succinate yield as a result of each incremental addition of mutation to the parental strain. Yield is mole of succinate produced per mole of glucose consumed. Mean and standard deviation were calculated based on duplicate experiments.
Figure 9:
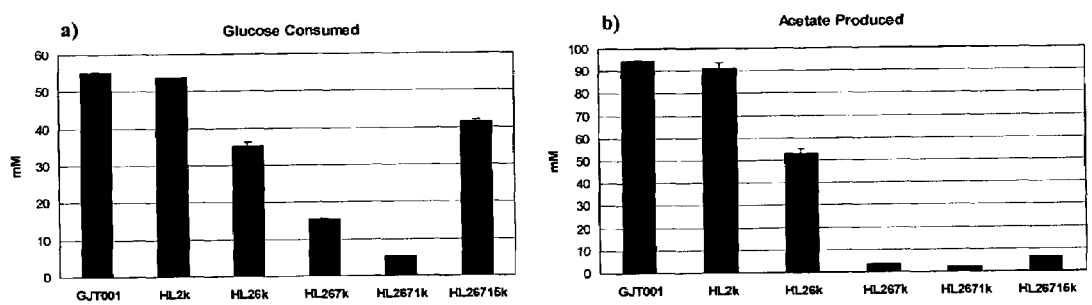
FIG. 9 Glucose and Acetate Metabolism. a) Glucose consumed after 24 hours of culture; b) Acetate produced after 24 hours of culture. Mean and standard deviation were calculated based on duplicate experiments.
Figure 10:
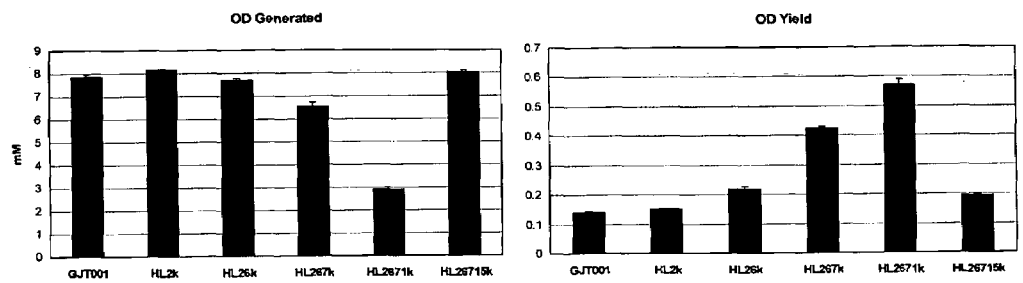
FIG. 10 Growth in Standard Media. a) Growth after 24 hours. OD measured at 600 nm.; b) OD yield ($OD_{600}$/mole glucose) after 24 hours of culture. Mean and standard deviation were calculated based on duplicate experiments.
Figure 11:
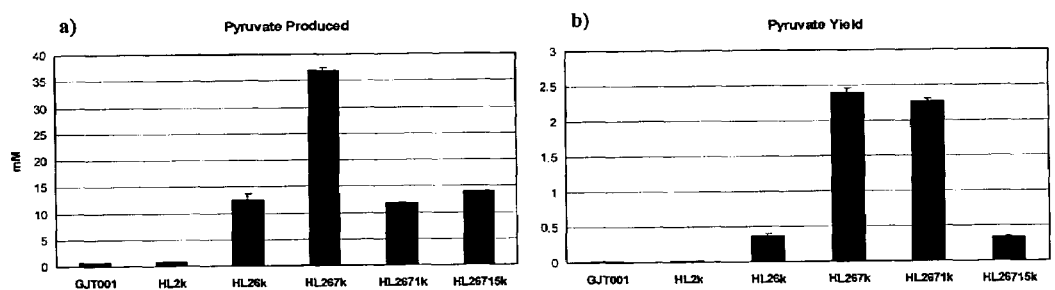
FIG. 11 Pyruvate Metabolism. a) Pyruvate accumulation after 24 hours of culture.; b) Pyruvate yield (mole pyruvate/mole glucose) after 24 hours of culture. Mean and standard deviation were calculated based on duplicate experiments.

FIGS. 8 and 9 show succinate production and yield from cultures of each mutant strain and the parental strain. In the mutant strain HL2k, with only sdh inactivated, succinate accumulated during culture. Succinate accumulation was not possible in the wildtype (GJT001) as shown by zero succinate production (FIG. 8a). Inactivation of the two acetate pathways, poxB and ackA-pta, further increased succinate production and yield as shown by mutant strain HL267k. Next, as dictated by the design strategy, icd was inactivated creating mutant strain HL2671k. When the icd was inactivated, succinate production decreased as expected since the cell probably could no longer use the oxidative arm of the TCA cycle to produce succinate. The amount of succinate produced by HL2671k could be due to the glyoxylate bypass being partially active. The molar succinate yield of HL2671k increased significantly but this was accompanied by a much lower glucose consumption (FIG. 9a). Finally, when the glyoxylate bypass was activated by inactivating iclR, succinate production increased substantially to 14.28 mM with a molar yield of 0.344. This is over a 5-fold increase in succinate production compared to HL2671k. The result is shown by the pentamutant strain HL26715k. At this point, a highly functioning glyoxylate cycle is created, which provides a detour to relieve the carbon flux from the TCA cycle bottleneck created in mutant strain HL2671k. Activating the glyoxylate bypass reconstituted the cycling and replenishment of OAA. As a result, HL26715k showed much higher glucose consumption than the previous three strains containing mutations due to a faster and more efficient carbon throughput (FIG. 8a). The cell growth of HL26715k was also healthy again, and was similar to that of the wildtype parental strain GJT001 (FIG. 10a). This aerobic succinate production system serves as a novel platform metabolic engineering improvements on succinate production in E. coli.

EXAMPLE 2

Succinate Production Through Glyoxylate Shunt

Figure 3:
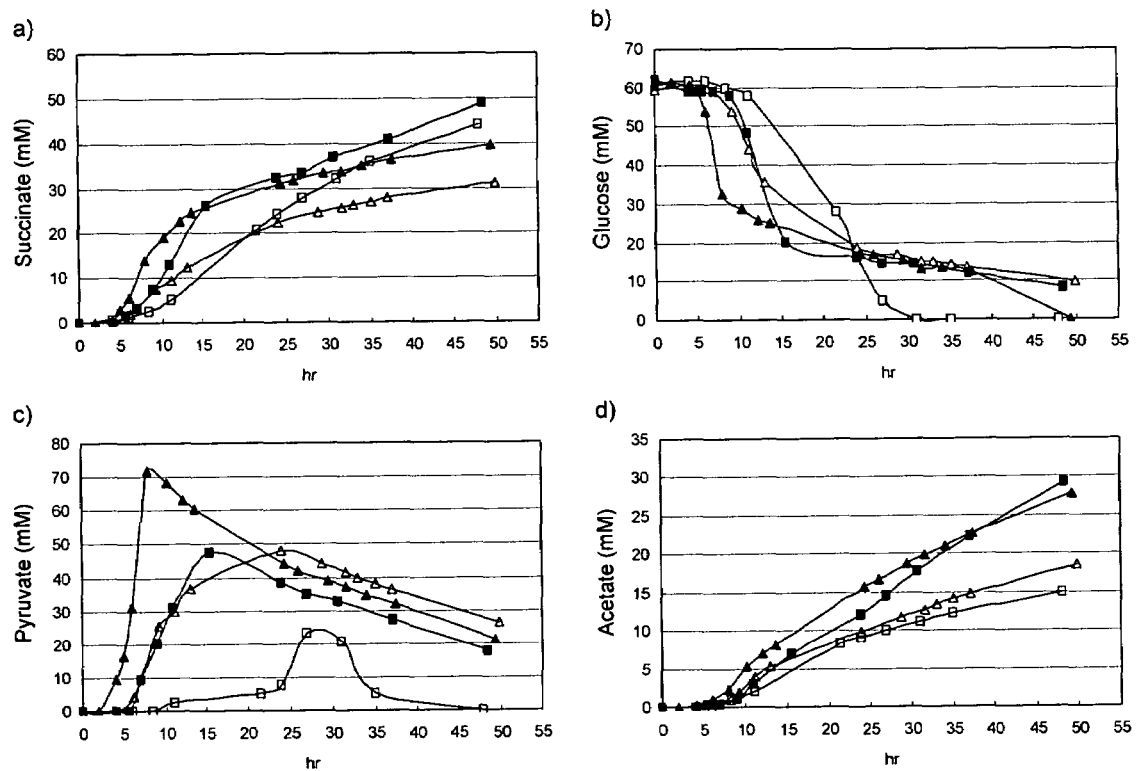
FIG. 3 Metabolite Production with Glyoxylate Shunt. a) Succinate production; b) Glucose remaining; c) Pyruvate production; d) Acetate production. Solid square (■) is HL27659k; solid triangle (▲) is HL2765k; open square (□) is HL512769k; open triangle (△) is HL51276k. Cultivation medium is LB with 2 g/L NaHCO3 and approximately 60 mM of glucose FIG. 4 Pentamutant HL51276k with Sorghum PEPC. a) Succinate production; b) Glucose remaining; c) Pyruvate production; d) Acetate production. Solid diamond (◆) is HL51276k(pKK313); solid square (■) is HL51276k (pKK313C). Cultivation medium is LB with 2 g/L NaHCO3 and approximately 60 mM of glucose.

Mutant strains HL51276k and HL2765k were generated which removed acetate production through acetate kinase-phosphotransacetylase (ackA-pta) and pyruvate oxidase (poxB). Succinate dehydrogenase (sdh) was deleted to prevent the formation of downstream Krebs cycle intermediates. Isocitrate lyase (aceA) repression was removed to allow constitutive activation of the aceBAK operon producing excessive amount of isocitrate lyase and malate synthase. Additionally, isocitrate dehydrogenase was removed from HL51276k to prevent the upstream production of 2-ketoglutarate. Results (Table 3) showed that strain HL2765k had a higher succinate production than HL51276k. At approximately 48 hours, the succinate concentration in the HL2765k culture was 40 mM compared to 31 mM succinate produced by the HL51276k culture (FIG. 3a). Succinate molar yields at the highest concentration produced were 0.67 for HL2765k and 0.65 for HL51276k. HL2765k also had 65% higher volumetric succinate productivity and 12% higher specific succinate productivity than HL51276k. Strain HL2765k grew to a higher OD (14.27 OD) than strain HL51276k (9.21 OD). HL2765k also had a faster biomass generation rate (0.60 g/l-hr) than HL51276k (0.24 g/l-hr), because its glucose consumption rate is faster than HL51276k.

TABLE 3

Succinate production through Glyoxylate Shunt.

| Strain | $Y_{S/G}$ [a] (mol/mol) | $Q_p$ [b] (g/l-hr) | $q_p$ [c] (mg/g-hr) |
|---|---|---|---|
| HL51276k | 0.65 | 0.057 | 24.04 |
| HL512769k | 0.87 | 0.086 | 35.47 |
| HL2765k | 0.67 | 0.094 | 26.84 |
| HL27659k | 0.78 | 0.130 | 32.82 |
| HL51276k(pKK313C) | 0.61 | 0.048 | 27.54 |
| HL51276k(pKK313) | 1.09 | 0.140 | 44.26 |
| HL512769k(pKK313C) | 0.85 | 0.083 | 38.99 |
| HL512769k(pKK313) | 0.96 | 0.094 | 45.23 |
| HL2765k(pKK313C) | 0.71 | 0.113 | 28.33 |
| HL2765k(pKK313) | 0.75 | 0.111 | 35.54 |
| HL27659k(pKK313C) | 0.74 | 0.106 | 31.14 |
| HL27659k(pKK313) | 0.95 | 0.270 | 73.66 |

[a]$Y_{S/G}$ is molar succinate yield (mole succinate/mole glucose)
[b]$Q_p$ is volumetric succinate productivity (concentration of succinate (g/l) per hour)
[c]$q_p$ is specific succinate productivity (mass of succinate (mg) per biomass (g) per hour)

Both strains produced significant amounts of succinate, but HL2765k was more robust than HL51276k. Strain HL2765k with two pathways engineered for succinate production has a more rapid succinate production and glucose consumption rate than HL51276k, which only utilizes the glyoxylate cycle for succinate production.

EXAMPLE 3

Removing Glucose Transport

Figure 4:
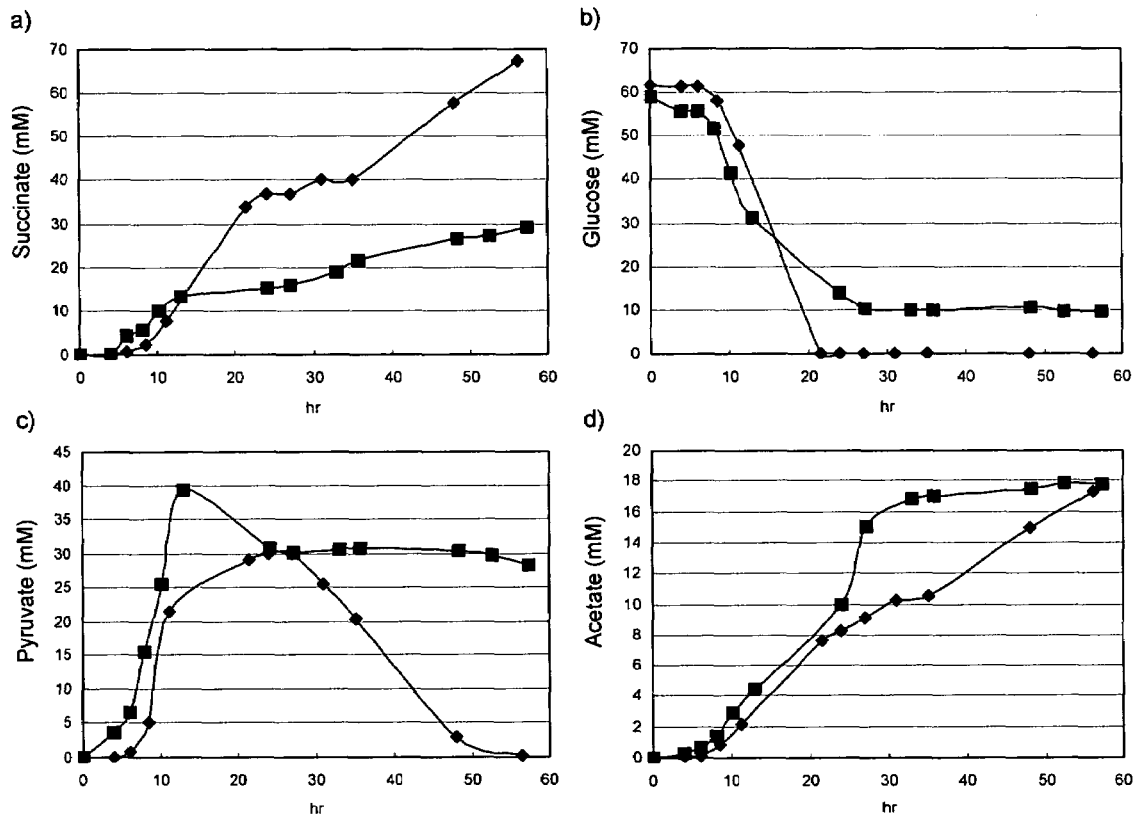
Figure 5:
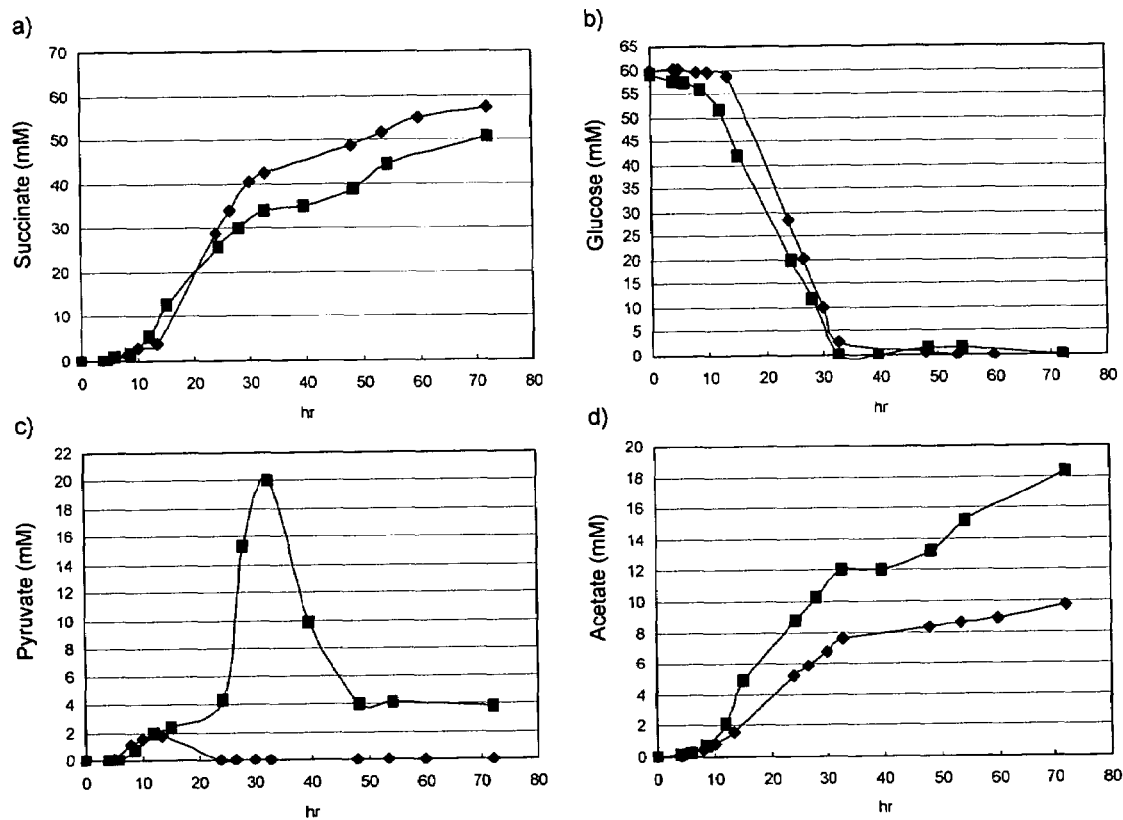
FIG. 5 Hexamutant HL512769k with Sorghum PEPC. a) Succinate production; b) Glucose remaining; c) Pyruvate production; d) Acetate production. Solid diamond (◆) is HL512769k(pKK313); solid square (■) is HL512769k (pKK313C). Cultivation medium is LB with 2 g/L NaHCO3 and approximately 60 mM of glucose.
Figure 6:
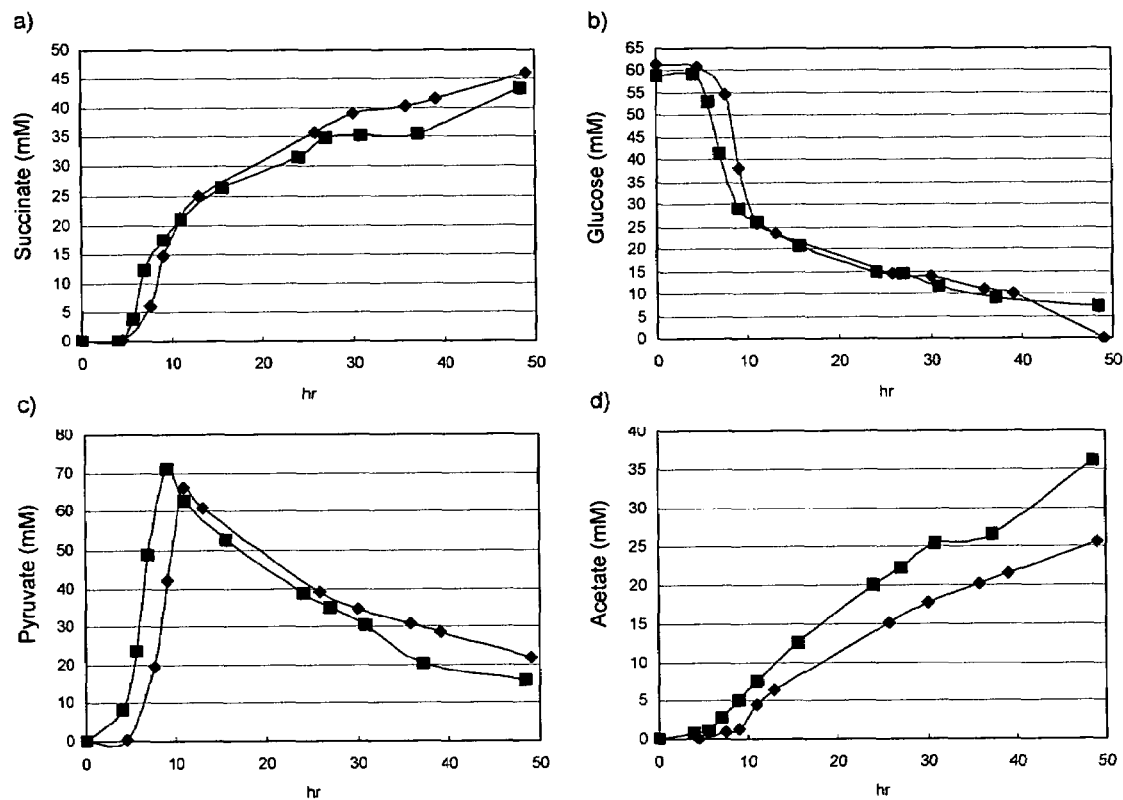
FIG. 6 Quadrimutant HL2765k with Sorghum PEPC. a) Succinate production; b) Glucose remaining; c) Pyruvate production; d) Acetate production. Solid diamond (◆) is HL2765k(pKK313); solid square (■) is HL2765k (pKK313C). Cultivation medium is LB with 2 g/L NaHCO3 and approximately 60 mM of glucose.
Figure 7:
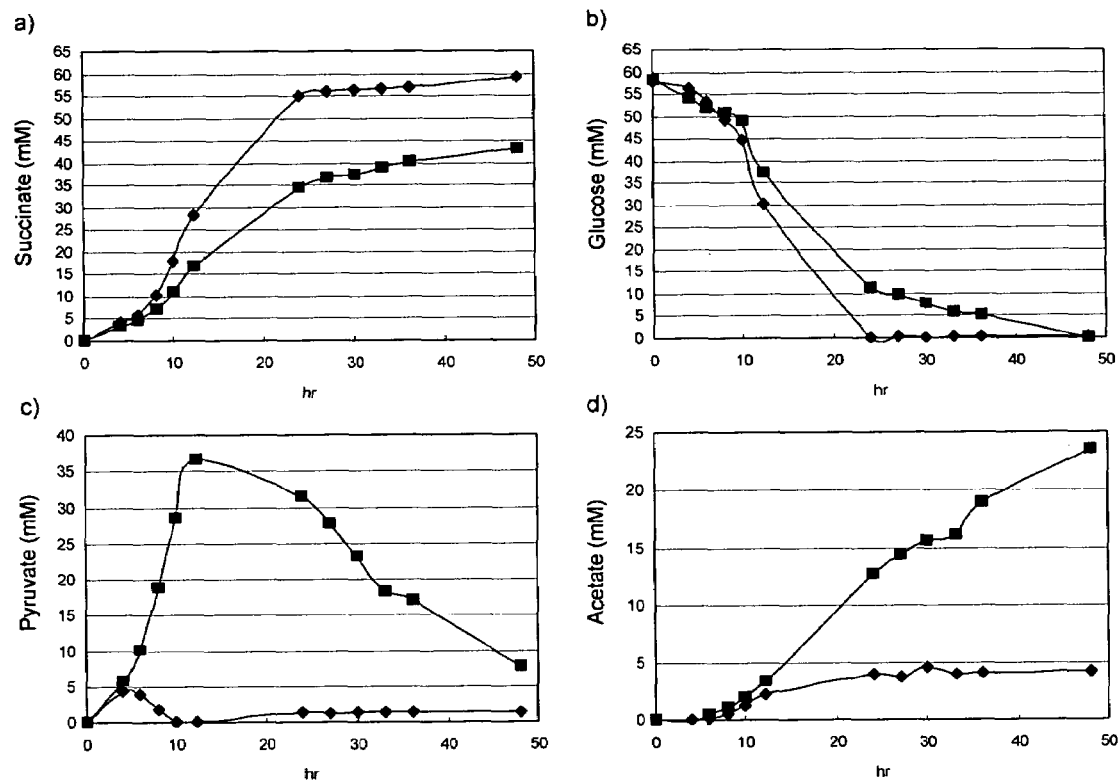
FIG. 7 Pentamutant HL27659k with Sorghum PEPC. a) Succinate production; b) Glucose remaining; c) Pyruvate production; d) Acetate production. Solid diamond (◆) is HL27659k(pKK313); solid square (■) is HL27659k (pKK313C). Cultivation medium is LB with 2 g/L NaHCO3 and approximately 60 mM of glucose.

Inactivation glucose phosphotransferase system (PTSG) was studied in HL2765k and HL51276k by knocking out ptsG to form HL27659k and HL512769k (hexamutant strain of E. coli). Strains HL27659k and HL512769k were grown aerobically under batch reactor conditions previously described. At approximately 48 hours, HL27659k produced 49 mM succinate over 40 mM produced by HL2765k and HL512769k produced 44 mM succinate over 31 mM produced by HL51276k (FIG. 4a). PTSG inactivation increased molar yield from 0.67 for HL2765k to 0.78 for HL27659k and from 0.65 for HL51276k to 0.87 for HL512769k. Volumetric succinate productivity was increased 38% and specific productivity 22% for HL27659k over HL2765k. HL512769k had 51% higher succinate volumetric productivity and 48% higher specific productivity than HL51276k. Inactivation of PTSG caused a decrease in cell growth due to slower glucose consumption. The biomass generation rate of strain HL2765k was 0.60 g/l-hr compared to strain HL27659k, which was 0.27 g/l-hr. For strain HL51276k, the biomass generation rate at the end of the exponential phase was 0.24 g/l-hr compared to strain HL512769k, which has 0.13 g/l-hr. The effects of ptsG inactivation improve succinate production more in HL51276k than in HL2765k; this is because there are more bottlenecks in the TCA pathways of HL51276k than in HL2765k.

Inactivation of ptsG reduces pyruvate and acetate accumulation in cultures of strains HL2765k and HL51276k (FIG. 4C). In strain HL512769k, there was no pyruvate accumulation after 48 hours. Complete glucose consumption was achieved by cultures of all four strains at the end of fermentation. In conclusion, inactivation of the glucose phosphotransferase system did improve succinate yield and productivity in HL2765k and HL51276k. Because of the ptsG inactivation, glucose consumption was slowed, pyruvate and acetate accumulation was reduced, a more balanced metabolism was obtained and increased succinate production was achieved.

EXAMPLE 4

Overexpression of PEPC

Figure 2:
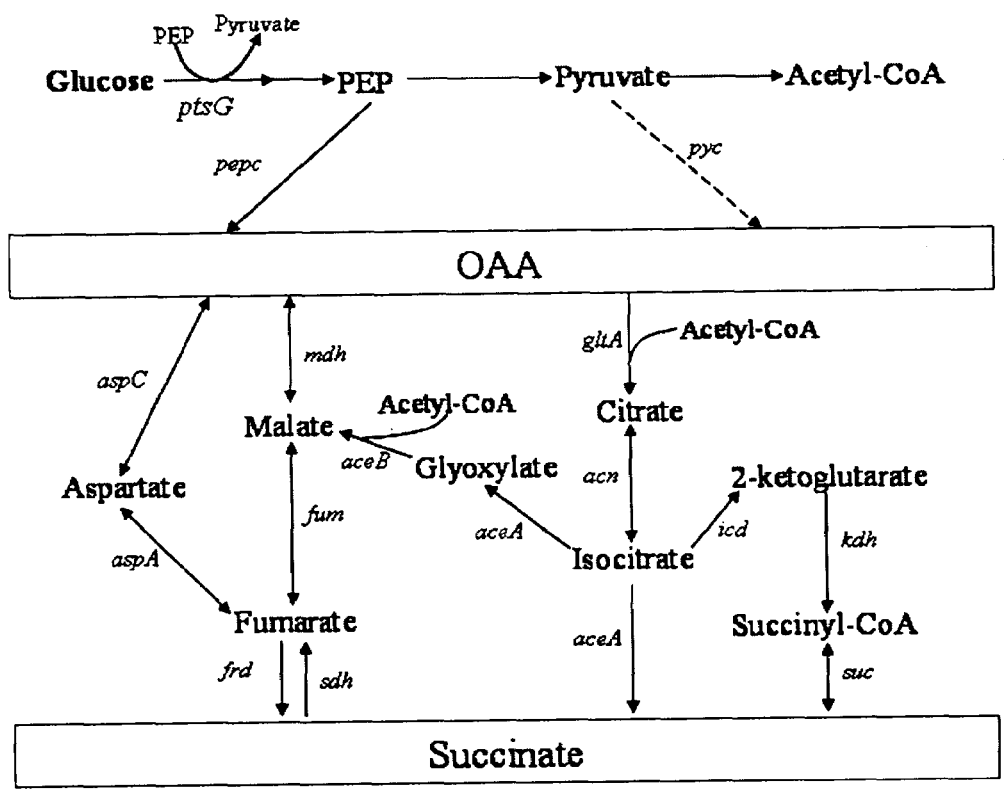
FIG. 2 Model network of succinate synthesis pathways. The pyruvate carboxylase (pyc) pathway is not indigenous in E. coli.

Although PTSG inactivation in strains HL27659k and HL512769k increased succinate production, it may still be theoretically possible to obtain greater succinate production and better yield per mole glucose. To further optimize succinate production, PEPC was used to convert PEP to OAA which can be converted to succinate as a TCA intermediate and source of citrate for the glyoxylate shunt (FIGS. 1 and 2). The S8D mutant PEPC from Sorghum was overexpressed on plasmid pKK313 in the four strains HL51276k, HL512769k, HL2765k, and HL27659k. The S8D mutant is feedback inhibition resistant to malate (56). The mutant strains carrying the plasmids were grown aerobically in bioreactors as previously described. Mutant strains harboring pKK313 were compared to the same mutant strains harboring the pKK313C control vector.

Overexpression of the mutant Sorghum PEPC in strains HL51276k, HL512769k, HL2765k, and HL27659k was effective in increasing succinate production (FIG. 4-7). The succinate production in bacterial strains HL2765k (pKK313), HL51276k(pKK313), HL27659k(pKK313), and HL512769k(pKK313) was continuously higher than control strains HL2765k(pKK313C), HL51276k(pKK313C), HL27659k(pKK313C), and HL512769k (pKK313C) throughout the production phase (FIGS. 6a and 7a). In strains with high levels of PEPC, the molar succinate yields for strains HL51276k(pKK313), HL512769k(pKK313) and HL27659k(pKK313) all reached the maximum theoretical value of 1 mole of succinate produced per mole of glucose consumed (Table 3). The molar succinate yield for HL2765 (pKK313) was 0.75 succinate/glucose. HL27659(pKK313) produced 60 mM succinate for a yield of 1 mole succinate per mole glucose.

These results demostrated that high expression of mutant Sorghum PEPC was very effective in improving succinate yield in the mutant E. coli host strains and optimized the aerobic production systems to produce the maximum theoretical succinate yield of 1 mole per 1 mole glucose consumed. HL27659k(pKK313) was the most efficient with little acetate or pyruvate produced. None of the PEPC expressing cultures produced any detectable levels of lactate or ethanol. These results further demonstrate that aerobic bacterial fermentation provides a robust and efficient aerobic succinate production system for large-scale carboxylic acid production. Further, these results demonstrate that overexpression of pepc coupled with ptsG inactivation was very effective in reducing pyruvate and acetate accumulation, thus providing efficient carbon throughput for succinate production.

EXAMPLE 5

Batch Reactor Growth

Figure 12:
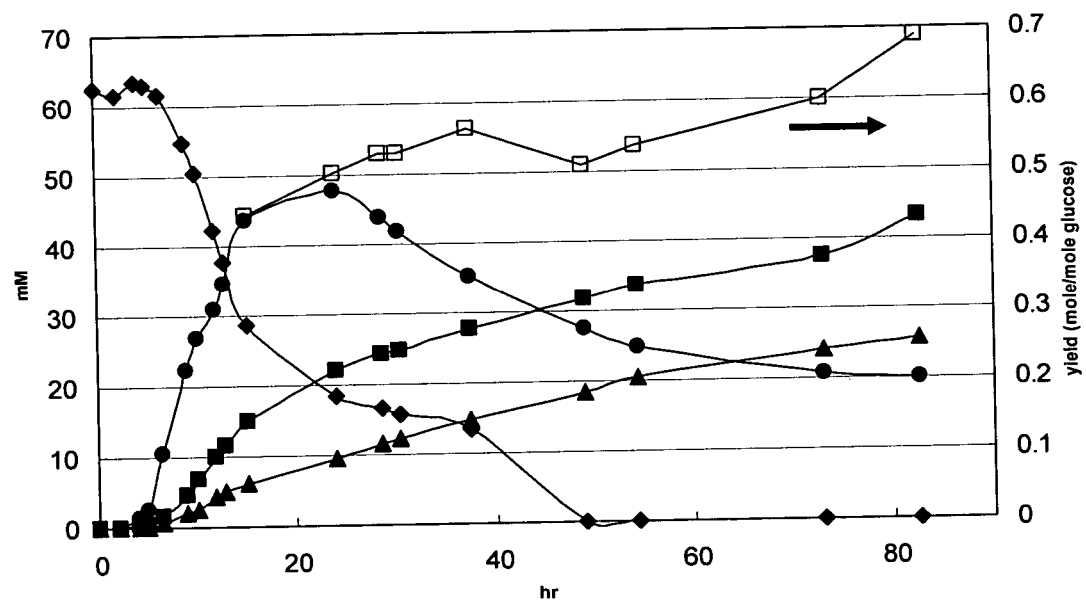
FIG. 12 Aerobic Bioreactor with Pentamutant HL27615k. Solid diamond (◆) is glucose consumed. Solid square (■) is succinate produced. Solid triangle (▲) is acetate produced. Solid circle (●) is pyruvate produced. Open square (□) is the succinate yield (mole succinate produced per mole glucose consumed).
Figure 13:
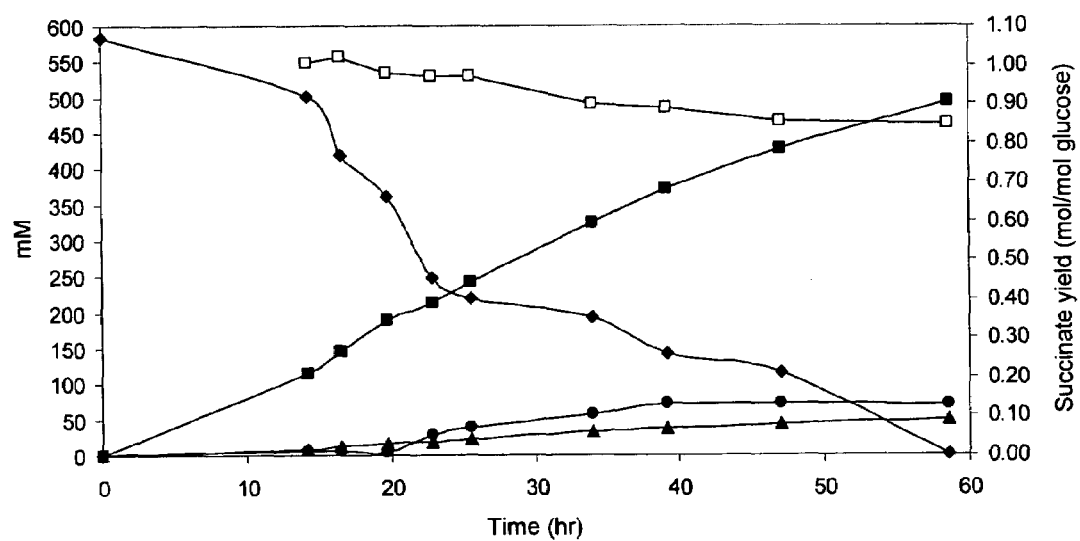
FIG. 13 Aerobic Fed-Batch Reactor with HL27659k (pKK313). Glucose (mM) (◆), succinate (mM) (■), pyruvate (mM) (●), acetate (mM) (▲), and succinate yield (mol/mol glucose) (□) are shown.

In FIG. 12, an aerobic batch reactor was used to control oxygen and substrate concentration. The pentamutant strain, HL27615k, was characterized under controlled conditions in an aerobic batch reactor. This demonstrates the use of aerobic succinate production system in an industrial setting. In the bioreactor, 63 mM of glucose was added and 1% inoculum from an overnight culture grown from a single colony was used. Temperature and pH were maintained at 37° C. and 7.0, respectively. The DO was maintained above 80% saturation.

A bioreactor generates higher productivity due to a more controlled environment. The results show that at 24 hours, succinate production is 22 mM with a molar yield of 0.5 (FIG. 12). This is better than the results from flask studies at 24 hours, which were 14 mM of succinate with a yield of 0.34. Cells reached maximum OD of 9.12 after 12 hours with a specific growth rate of approximately 0.45 hr$^{-1}$. At 24 hours, pyruvate accumulation reached a maximum of 48 mM and glucose consumed was 44 mM. After 24 hours, the cells started consuming the excreted pyruvate along with the remaining glucose. All the glucose was consumed by about 49 hours at which point the pyruvate was still being consumed. By 83 hours, the pyruvate was not completely consumed, but succinate production reached 43 mM with a yield of 0.7. There was also accumulation of TCA cycle C6 intermediates, which had not been consumed by the cells (data not shown). The results of the batch reactor study show that the pentamutant strain HL27615k has the potential to produce a large quantity of succinate under absolute aerobic conditions, and that there is potential to achieve the maximum succinate theoretical yield of 1.0.

EXAMPLE 6

Chemostat Reactor Growth

To further control culture conditions and improve succinate productivity, a chemostat reactor was used to culture the mutant strains under aerobic conditions (data not shown). The production of succinate, pyruvate, and acetate under aerobic conditions was compared between the five mutant strains HL27659k, HL2765k, HL276k, HL2761k, and HL51276k in chemostat cultures at 0.1 hr$^{-1}$ dilution rate. The biomass concentrations of the five mutant strains were HL27659k (3.4 g/L), HL2765k (3.6 g/L), HL276k (3.4 g/L), HL2761k (2.4 g/L) and HL51276k (2.6 g/L). Succinate production reached substantial levels that were similar in strains HL27659k, HL2765k, and HL276k. Strain HL27659k produced 57 mM of succinate, strain HL2765k produced 61 mM, and strain HL276k produced 58 mM. Succinate production was significantly lower for strains HL2761k and HL51276k than the other three strains. Strain HL2761k only produced 2 mM of succinate and strain HL51276k produced only 3 mM of succinate. Strain HL27659k achieved the highest succinate yield among all the strains. It obtained 0.91 mole succinate per mole glucose. This is 91% of the maximum theoretical succinate yield, which is 1.0 mol/mol glucose under aerobic conditions. Controlling reactor conditions to maintain a constant chemical and aerobic environment can be used to further increase carboxylic acid yield from these cultures.

REFERENCES

All of the references cited herein are expressly incorporated by reference. References are listed again here for convenience:

1. Amann, et al., Gene 69:301-15 (1988)
2. Ausebel, "Current Protocols in Molecular Biology" Greene Pub. Assoc.

3. Berrios-Rivera, et al. Metab Eng. 4:217-29 (2002).
4. Carole, et al. Appl Biochem Biotechnol. 113-116:871-85 (2004).
5. Cecchini, et al., (Bray, et al., eds) pp. 555-558, Walter de Gruyter, New York (1984).
6. Chan and Sim, Microbiology 144:3229-37 (1998).
7. Chang, et al. Appl Environ Microbiol. 65:1384-9 (1999).
8. Chatterjee, et al. Appl Environ Microbiol. 67:148-54 (2001).
9. Datsenko and Wanner. Proc Natl Acad Sci USA. 97:6640-5 (2000).
10. Dittrich, et al. Biotechnol. Prog. 21:627-31 (2005).
11. Fiegler, et al., J. Bact. 181:4929-36 (1999).
12. Fujii, et al., Appl. Environ. Microbiol. 60:2786-92 (1994).
13. Gokarn, et al., Biotech. Let. 20:795-8 (1998).
14. Gokarn, et al., Appl. Environ. Microbiol. 66:1844-50 (2000)
15. Gokarn, et al., App. Microbiol. Biotechnol. 56:188-95 (2001)
16. Goldberg, et al., App. Environ. Microbiol. 45:1838-47 (1983).
17. Hahm, et al., Appl. Microbiol. Biotechnol. 42:100-7 (1994).
18. Hari Krishna, et al., J. Biotechnol. 87:193-201 (2001).
19. Hasona, et al. J Bact. 186:7593-600 (2004).
20. Holms, Curr. Top. Cell Regul., 28:69-105 (1986).
21. Hong and Lee, Appl. Microbiol. Biotechnol. 58:286-90 (2002).
22. Horton, et al., J. Ind. Microbiol. Biotechnol. 30:427-32 (2003).
23. Kelly, et al., Microbiology 148:793-8 (2002).
24. Kern, et al., FEMS Yeast Research. 5:43-9 (2004).
25. Kim, et al. Appl Environ Microbiol. 70:1238-41 (2004).
26. Kornberg, Biochem. J. 99:1-11 (1966).
27. Lehninger, et al. "Principles of Biochemistry, $2^{nd}$ ed." Worth Pub., New York (1993).
28. Lin, et al. Biotechnol. Prog. 20:1599-604 (2004).
29. Lin, et al. Biotechnol. Bioeng. 89:148-56 (2005).
30. Lin, H. "Metabolic Network Design and Engineering in E. coli" Ph.D. Thesis, Rice University, Dept. of Bioengineering (2005).
31. Lin, et al. J. Ind. Microbiol. Biotechnol. 32:87-93 (2005).
32. Lin, et al. Metab. Eng. 7:116-27 (2005).
33. Lin, et al. Appl. Microbiol. Biotechnol. 67:515-23 (2005).
34. Lin, et al. Biotechnol. Bioeng. 90:775-9 (2005).
35. Lin, et al. Biotechnol. Prog. 20:1599-604 (2004).
36. Luli and Strohl, Appl. Environ. Microbiol. 56:1004-11 (1990).
37. Maklashina, et al. J Bact. 180:5989-96 (1998).
38. Millard, et al.,. App. Environ. Microbiol. 62:1808-10 (1996).
39. Nagasawa, et al. Biosci. Biotech. Biochem. 62:1852-7 (1998).
40. Phillips, et al., Biotechniques. 28:400-8 (2000).
41. Sambrook, Fritsch, and Maniatis, "Molecular Cloning—A Laboratory Manual, 2nd ed." Cold Spring Harbor Laboratory, New York (1989).
42. Samuelov, et al. Appl Environ Microbiol. 65:2260-3 (1999).
43. Sanchez, et al. Biotechnol. Prog. 21:358-65 (2005a).
44. Sanchez, et al., Metab. Eng. 7:229-39 (2005b).
45. Stols and Donnelly App. Environ. Microbiol. 63:2695-701 (1997).
46. Tolentino et al., Biotech. Let. 14:157-62. (1992).
47. Underwood, et al., App. Environ. Microbiol. 68:1071-81 (2002).
48. Vadali, et al., Metab. Eng. 6:294-9 (2004a).
49. Vadali, et al., Biotechnol. Prog. 20:692-7 (2004b).
50. Vadali, et al., Appl. Microbiol. Biotechnol. 63:698-704 (2004c).
51. Varadarajan and Miller, Biotechnol. Prog. 15:845-854 (1999).
52. Vemuri, et al., Appl. Environ. Microbiol. 68:1715-1727 (2002).
53. Vemuri, et al. J. Ind. Microbiol. Biotechnol. 28:325-32 (2002).
54. Voet and Voet, "Biochemistry $2^{nd}$ ed." John Wiley & Sons, New York (1995).
55. Volkert, et al., J. Bact. 176:1297-302 (1994).
56. Wang, et al., J. Biol. Chem. 267:16759-62. (1992)
57. Wang, et al. App. Biochem. Biotechnol. 70-72:919-28 (1998).
58. Wang, et al., App. Environ. Microbiol. 66:1223-7 (2000).
59. Xu, et al. Biotechnol. Prog. 15:81-90 (1999).
60. Xu, et al. Appl. Microbiol. Biotechnol. 51:564-71 (1999).
61. Yang, et al. Biotechnol. Bioeng. 65:291-7 (1999).
62. Yang et al., Metab. Eng. 1, 141-152 (1999b).
63. Yanisch-Perron, et al., Gene 33:103-19 (1985).
64. Yoshimoto, et al. Yeast. 15:409-17 (1999).
65. Yoshioka and Hashimoto. Agric Biol. Chem. 45:2183-90 (1981).
66. Zeikus, et al., App. Microbiol. Biotechnol. 51:545-52 (1999).
67. Zhang, et al. Sheng Wu Gong Cheng Xue Bao. 17:59-63 (2001).

The invention claimed is:

1. A method of aerobically producing succinate comprising:
   a) generating a genetically engineered *E. coli* strain comprising:
      i) reduced activity of succinate dehydrogenase (sdhAB), acetate kinase (ackA), phosphotransacetylase (pta) or both ackA-pta, and
      ii) reduced activity of pyruvate oxidase (poxB); and
      iii) reduced activity of aceBAK operon repressor (iclR); and
      iv) reduced activity of phosphotransferase system gene (ptsG), and
      v) increased activity of phosphoenolpyruvate carboxylase (pepc); and
   b) culturing said bacteria in a fed-batch reactor so that said bacteria produce at least 500 mM succinate.

2. The method of claim 1, wherein said bacterial strain comprises a deletion of one or more genes selected from the group consisting of sdh, ackA, pta, poxB, iclR and ptsG.

3. The method of claim 1, wherein said bacterial strain comprises a knockout of one or more genes selected from the group consisting of sdh, ackA, pta, poxB, iclR and ptsG.

4. The method of claim 1, wherein said bacterial strain further comprises an expression vector encoding pepc.

* * * * *

UNITED STATES PATENT AND TRADEMARK OFFICE
CERTIFICATE OF CORRECTION

PATENT NO. : 7,262,046 B2
APPLICATION NO. : 11/200385
DATED : August 28, 2007
INVENTOR(S) : Ka-Yiu San, George N. Bennett and Henry Lin It is certified that error appears in the above-identified patent and that said Letters Patent is hereby corrected as shown below:

On the Title Pg, replace the Item (75) Inventor, "San Ka-Yiu" with --Ka-Yiu San--.

Signed and Sealed this

Thirtieth Day of June, 2009

JOHN DOLL
*Acting Director of the United States Patent and Trademark Office*